United States Patent

Becourt et al.

[11] Patent Number: 5,707,651
[45] Date of Patent: Jan. 13, 1998

[54] SOFT CAPSULES CONTAINING DINREBURNAMENINE COMPOUNDS

[75] Inventors: Philippe Becourt, Massy; Jean-Luc Dubois, Paris; Pierre Metziger, Lampertheim, all of France

[73] Assignee: Roussel Uclaf, France

[21] Appl. No.: 608,284

[22] Filed: Feb. 28, 1996

[30] Foreign Application Priority Data

Mar. 3, 1995 [FR] France ................... 95 02482

[51] Int. Cl.$^6$ .................................. A61K 9/48
[52] U.S. Cl. ........................... 424/451; 424/456
[58] Field of Search .............. 546/57; 424/456, 424/451

[56] References Cited

U.S. PATENT DOCUMENTS

| | | | |
|---|---|---|---|
| 4,486,412 | 12/1984 | Shah et al. | 424/156 |
| 5,093,337 | 3/1992 | Aktogu et al. | 514/283 |
| 5,178,877 | 1/1993 | Garren et al. | 424/456 |
| 5,324,280 | 6/1994 | Wong et al. | 604/892.1 |
| 5,332,748 | 7/1994 | Aktogu et al. | 514/283 |
| 5,413,572 | 5/1995 | Wong et al. | 604/892.1 |

FOREIGN PATENT DOCUMENTS

| | | |
|---|---|---|
| 2381048 | 9/1978 | European Pat. Off. . |
| 0317427 | 5/1989 | European Pat. Off. . |
| 0427998 | 5/1991 | European Pat. Off. . |

*Primary Examiner*—Thurman K. Page
*Assistant Examiner*—Sharon Howard
*Attorney, Agent, or Firm*—Bierman, Muserlian & Lucas

[57] ABSTRACT

A soft capsule containing a) a capsule casing containing gelatin and optionally a plasticizer and other additives, b) a compound of the formula

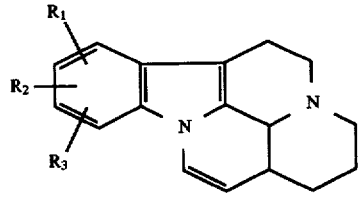

wherein $R_1$, $R_2$ and $R_3$ are individually selected from the group consisting of hydrogen, halogen, alkyl and alkoxy of 1 to 5 carbon atoms, —OH, —CF3, —NO2, —NH2, alkylamino and dialkylamino of 1 to 5 alkyl carbon atoms and acylamino of acyl of an aliphatic carboxylic acid of 1 to 6 carbon atoms or a non-toxic, pharmaceutically acceptable acid addition salt thereof and c) at least one mineral oil and optionally a pharmaceutical carrier.

7 Claims, No Drawings

SOFT CAPSULES CONTAINING DINREBURNAMENINE COMPOUNDS

STATE OF THE ART

The compounds of formula I are known and the preferred products are described in U.S. Pat. No. 5,093,337 and their non-toxic, pharmaceutically acceptable acid addition salts. The said compounds have useful pharmacological properties, and notably nootropic, anti-depressive, neuronal protective, anti-anoxic or anti-ischemic properties. Certain products have an affinity for the alpha 2 adrenergic receptors and can be used for the treatment of Alzheimer's disease.

These active ingredients are compounds which are unstable and very sensitive to humidity and to oxidation. Moreover, the active ingredient has shown itself to be incompatible with most of the excipients normally used in the formulation of pharmaceutical compositions. It therefore appeared judicious to find a new formulation for these active ingredients, providing them with an improved stability.

OBJECTS OF THE INVENTION

It is an object of the invention to provide soft capsules containing dinoreburnamenine compounds of formula I which are stable and a process of their preparation.

These and other objects and advantages of the invention will become obvious from the following detailed description.

THE INVENTION

The soft capsules of the invention are comprised of a) a capsule casing containing gelatin and optionally a plasticizer and other additives, b) a compound of the formula

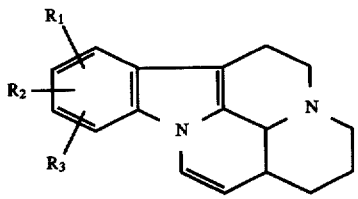

I wherein R1, R2 and R3 are individually selected from the group consisting of hydrogen, halogen, alkyl and alkoxy of 1 to 5 carbon atoms, —OH, —CF3, —NO2, —NH2, alkylamino and dialkylamino of 1 to 5 alkyl carbon atoms and acylamino of acyl of an aliphatic carboxylic acid of 1 to 6 carbon atoms or a non-toxic, pharmaceutically acceptable acid addition salt thereof and c) at least one mineral oil and optionally a pharmaceutical carrier. The compound of formula I is a suspension or a solution with at least one mineral oil.

The capsule casing is made of gelatin, and optionally other additives such as coloring agents, a plasticizer or sugars. The casing can contain a small quantity of water and silicone fluids and/or glycerol oils can also be used in this casing.

The mixture for filling the capsule contains the active ingredient, the mineral oil as well as optionally other additives selected from known substances which do not alter the active ingredient. The invention also relates to a process for preparing such soft gelatin capsules with the active ingredient. In principle, the preparation of gelatin capsules is well known. It is for example described in detail in a publication by Leon Lachmann of 1976 (The Theory and Practice of Industrial Pharmacy, Lea and Febiger, Philadelphia, 2nd edition, P. 404–420, 1976). This document teaches that the nature of the materials for filling soft capsules is essentially limited to three categories, namely a) supports which are non-miscible with water, b) non-volatile supports or c) slightly volatile supports such as oils, fats, ethereal oils, chlorinated hydrocarbons, esters, ethers, alcohols and higher organic acids.

Patent DE-A-33 07 353 describes a process for preparing soft gelatin capsules containing polyethylene glycol where the polyethyleneglycol can only be encapsulated in a reliable manner if well-defined parameters are fixed with regard to both the casing of the capsules and the substances of the mixture for filling the capsules. The problems relating to the encapsulation can be explained by the fact that fillers containing polyethyleneglycol have pronounced exchange effects on the capsule casings and therefore, the stability during storage of the capsules cannot be guaranteed.

U.S. Pat. No. 2,580,683 describes gelatin capsules which are filled with very concentrated solutions of hygroscopic substances such as glucose syrup. The mixture for filling the capsules is so concentrated in hygroscopic substance that the mixture for filling the capsules can no longer destroy the capsule casing.

Application EP-A 120 248 describes soft gelatin capsules containing polyethyleneglycol and processes for preparing them. Then, standard capsule casings are used and the mixture for filling the capsules is a solution or suspension of the active ingredient in polyethyleneglycol.

A preferred object of the invention is soft capsules comprising a capsule casing and a mixture for filling the capsule, characterized in that a) the capsule casing contains gelatin and optionally a plasticizer and other additives, b) the mixture for filling the capsule contains a compound of formula (I) or an addition salt with pharmaceutically acceptable mineral or organic acids of said compound of the formula

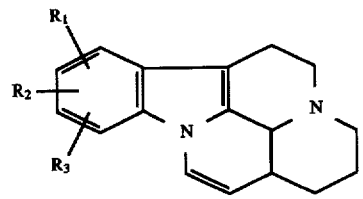

I wherein R1, R2 and R3 are individually hydrogen, halogen, alkyl or alkoxy of 1 to 5 carbon atoms, hydroxy, trifluoromethyl, nitro, amino, alkylamino and dialkylamino in which the alkyl has 1 to 5 carbon atoms, or acylamino in which the acyl is the remainder of an aliphatic carboxylic acid of up to 6 carbon atoms, and c) the mixture for filling the capsule also contains one or more by mineral oils.

In the soft capsules of the invention, the capsule casing preferably contains gelatin and a plasticizer chosen from known substances for standard capsule casings. More preferred are soft capsules as defined above in which the mixture for the capsule contains a compound of formula I or a pharmaceutically acceptable addition salt of said compound of formula I in which R1 and R2 are hydrogen and R3 is alkyl of 1 to 5 carbon atoms, particularly methyl or ethyl. R3 is preferably in position 11 of the heterocyclic system.

A more preferred object of the invention is a soft capsule which contains a compound of the formula (II) or an addition salt with pharmaceutically acceptable mineral or organic acids thereof:

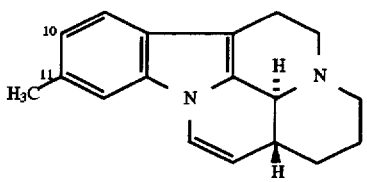

The fumarate or the maleate of the compound II, (3-α)-11-methyl-20,21-dinoreburnamenine, is preferred as the addition salt.

The mixture for filling the capsule contains, in addition to the active ingredient of formula I or II, at least one mineral oil. The filling mixture does not contain water, nor other solvents which could alter the active ingredient.

A particular subject of the invention are soft capsules as defined above in which the mixture for filling the capsule contains a compound of formula I and one or more substances selected from the group consisting of vaseline, vaseline oil and silicone fluid, preferably a combination of vaseline with vaseline oil and more preferably the mixture for filling the capsule contains 1 to 20% by weight of (3α)-11-methyl 20,21-dinoreburnamenine maleate or fumarate.

Also a subject of the invention is a process for preparing a soft capsule comprising a capsule casing and a mixture for filling the capsule, characterized in that:

a) a mixture for the capsule casing is prepared which contains gelatin and optionally a plasticizer and other additives, b) the mixture for filling the capsule is prepared which contains a compound of formula I as defined above or an addition salt with pharmaceutically acceptable mineral or organic acids of said compound of formula I and at least one mineral oil, and c) the casing is formed and filled with the filling mixture.

According to the process of the invention, a solution or suspension of the active ingredient is prepared with one or more mineral oils. After filling the capsules with the suspension or solution of active ingredient in mineral oil and drying them in the usual way, pharmaceutical compositions are obtained which can be used immediately.

As a pharmaceutical composition of the invention, an oral capsule of soft gelatin as defined above is preferred. Soft gelatin capsules are particularly important because they are notably used in the pharmaceutical sector to be swallowed without chewing. It is also possible to prepare soft capsules intended to be chewed. In addition, it is also possible in principle, by using additives for the capsule casings, to prepare hard gelatin capsules which are stable for a long period of time during storage despite their sensitive filling mixtures. Means for stabilizing the soft capsule casing are described for example in U.S. Pat. No. 4,804,542.

The invention also relates to the combination of a casing stabilized by the addition of additives such as starches with a filling mixture which contains the active ingredient and the mineral oil. Thus, it has been observed that the exchange effect between the capsule casing and the environment is considerably limited. The new capsules are considerably less likely to become sticky or soft, which can be explained by a reduced take-up of moisture from the environment.

To implement the process of the invention to produce gelatin capsules with the active product, the additives are added to the gelatin concoction in the form of a suspension or a solution.

The usual dose, variable according to the active ingredient used, the patient treated and the illness in question, can be, for example, from 0.1 to 200 mg, preferably 0.5 to 50 mg, per day when administered orally. A soft capsule may contain 0.5 to 50 mg of the active ingredient.

The preparation of the active ingredient is described in detail in U.S. Pat. No. 5,093,337.

In the following examples, there are described several preferred embodiments to illustrate the invention. However, it should be understood that the invention is not intended to be limited to the specific embodiments.

EXAMPLE 1

Preparation of a soft capsule with (3-α) 11-methyl-20,21-dinoreburnamenine maleate A) The medicinal liquid (filling mixture) with 1 per cent of the active ingredient was produced in the following manner: 5.0 g of (3-α) 11-methyl-20,21-dinoreburnamenine maleate were dispersed mechanically or by another appropriate means in a mixer to form a homogeneous mixture in 295 g of vaseline (see French Pharmacopeia, X, 1990) and 200 g of liquid vaseline oil (see European Pharmacopeia, 2nd Ed. and French Pharmacopeia, X, 1990).

B) In the same way, 263.5 g of gelatin (see European Pharmacopeia, 2nd Ed.) were intimately mixed with 102 g of glycerol and 59.5 g of silicone fluid (Dimethicone 1000 from Rhône Poulenc Rorer).

c) The capsules were made by simultaneous injection and sealing. The gelatin mixture maintained at a temperature of 60° to 70° C. was deposited on internally-cooled rotating drums as a film of gelatin which solidified. The two symmetrically-formed films passed between two half-capsule cellular molds where the medicinal liquid (i.e. the filling mixture) was injected using a positive displacement pump precisely adjusted to 117 microliters (corresponding to 100 mg) for oval capsules. The liquid pushed the gelatin film back into the cells. The pressure exerted by the two cylinders combined with an adequate heating temperature was such that the gelatin was sealed and cut out around each cell. The capsules were dried in a ventilated oven or by any other appropriate means.

EXAMPLE 2

Preparation of a soft capsule with (3-alpha) 11-methyl-20, 21-dinoreburnamenine maleate A) The medicinal liquid constituting the filling mixture with 20 per cent of the active ingredient was produced in the following manner: 100.0 g of (3-α) 11-methyl-20,21-dinoreburnamenine maleate were dispersed mechanically or by another appropriate means in a mixer to form a homogeneous mixture with 200 g of vaseline (see French Pharmacopeia, X, 1990) and 200 g of liquid vaseline oil (see European Pharmacopeia, 2nd Ed. and French Pharmacopeia, X, 1990).

B) In the same way, 263.5 g of gelatin (see European Pharmacopeia, 2nd Ed.) were intimately mixed with 102 g of glycerol and 59.5 g of silicone fluid (Dimethicone 1000 from Rhône Poulenc Rorer).

c) The capsules were made by simultaneous injection and sealing. The gelatin mixture maintained at a temperature of 60° C. was deposited on internally-cooled rotating drums as a gelatin film which solidified.

The two symmetrically-formed films passed between two half-capsule cellular molds where the medicinal liquid (the filling mixture) was injected using a positive displacement pump precisely adjusted to 117 microliters (corresponding to 100 mg) for oval capsules. The liquid pushed the gelatin film back into the cells. The pressure exerted by the two cylinders combined with an adequate heating temperature was such that the gelatin was sealed and cut out around each cell. The capsules are dried in an oven.

The stability of the soft capsules of different sizes and shapes of Examples 1 and 2 was tested at different temperatures. After 1 year at a temperature of 25° C., no significant alteration of the soft capsules or of the active ingredient (at a 0.2% detection threshold) was revealed.

Various modifications of the product and process of the invention may be made without departing from the spirit or scope thereof and it should be understood that the invention is intended to be limited only as defined in the appended claims.

What we claims is:

1. A soft capsule comprising a) a capsule casing containing gelatin and optionally a plasticizer and additives, b) a compound of the formula

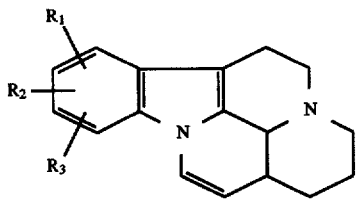

I wherein R1, R2 and R3 are individually selected from the group consisting of hydrogen, halogen, alkyl and alkoxy of 1 to 5 carbon atoms, —OH, CF3, —NO2, —NH2, alkylamino and dialkylamino of 1 to 5 alkyl carbon atoms and acylamino of acyl of an aliphatic carboxylic acid of 1 to 6 carbon atoms or a non-toxic, pharmaceutically acceptable acid addition salt thereof and c) at least one mineral oil and optionally a pharmaceutical carrier.

2. A soft capsule of claim 1, wherein R1 and R2 are hydrogen and R3 is alkyl of 1 to 5 carbon atoms.

3. A soft capsule of claim 1 wherein R1 and R2 are hydrogen and R3 is 11-methyl.

4. A soft capsule of claim 1 wherein components b) and c) are at least one member of the group consisting of vaseline, vaseline oil and silicone fluid.

5. A soft capsule of claim 1 containing a mixture of vaseline and vaseline oil.

6. A soft capsule of claim 1 containing 1 g to 20% by weight of (3α)11-methyl-20,21-dinoreburnamenine maleate or fumarate.

7. A process for the preparation process of soft capsules of claim 1 comprising forming a mixture of gelatin and optionally a plasticizer and additives, forming a capsule casing from said mixture and filling the soft capsule with a mixture of a compound of formula I of claim 1 and at least one mineral oil.

* * * * *